US008821476B2

(12) United States Patent
Agah et al.

(10) Patent No.: US 8,821,476 B2
(45) Date of Patent: Sep. 2, 2014

(54) DEVICES, METHODS AND KITS FOR DELIVERY OF THERAPEUTIC MATERIALS TO A PANCREAS

(75) Inventors: Ramtin Agah, Menlo Park, CA (US); Kamran Najmabadi, Palo Alto, CA (US)

(73) Assignee: RenovoRx, Inc., Palo Alto, CA (US)

( * ) Notice: Subject to any disclaimer, the term of this patent is extended or adjusted under 35 U.S.C. 154(b) by 785 days.

(21) Appl. No.: 12/958,711

(22) Filed: Dec. 2, 2010

(65) Prior Publication Data

US 2011/0295114 A1 Dec. 1, 2011

Related U.S. Application Data

(60) Provisional application No. 61/265,845, filed on Dec. 2, 2009.

(51) Int. Cl.
*A61M 25/00* (2006.01)
*A61M 29/00* (2006.01)
A61M 25/10 (2013.01)

(52) U.S. Cl.
CPC ....... *A61M 25/10* (2013.01); *A61M 2025/1015* (2013.01); *A61M 2025/1052* (2013.01); *A61M 2025/0037* (2013.01); *A61M 25/1011* (2013.01); *A61M 25/0097* (2013.01); *A61M 2025/0004* (2013.01); *A61M 25/007* (2013.01)
USPC ........................ 604/508; 604/101.04; 600/433

(58) Field of Classification Search
CPC ..... A61M 25/01; A61M 25/07; A61M 25/10; A61M 25/1011; A61M 2025/0004; A61M 2025/0006; A61M 2025/0039; A61M 2025/004; A61M 2025/1052; A61M 2025/1045; A61M 2210/12; A61M 2210/122; A61M 2025/104

USPC ......... 604/500, 507–510, 522, 96.01, 101.01, 604/101.02, 101.03, 101.04, 101.05, 604/103.01, 102.03, 103.03, 264, 915, 916, 604/917, 919; 600/433–435
See application file for complete search history.

(56) References Cited

U.S. PATENT DOCUMENTS

| 4,445,892 A | 5/1984 | Hussein et al. |
| 4,655,746 A | 4/1987 | Daniels et al. |

(Continued)

FOREIGN PATENT DOCUMENTS

| EP | 0 402 467 A1 | 12/1990 |
| EP | 0402467 A1 * | 12/1990 |

OTHER PUBLICATIONS

International Search Report and Written Opinion for PCT/US10/58684, mailed on Feb. 17, 2011; 11 pages.

(Continued)

*Primary Examiner* — Andrew Gilbert
(74) *Attorney, Agent, or Firm* — Cooley LLP

(57) ABSTRACT

Devices and methods are described herein for engraftment of stem cells into a pancreas using an endovascular approach. Targeted intra-arterial injection of stem cells selectively in a splenic artery can achieve engraftment of insulin producing cells in the tail of the pancreas with high efficiency and without systemic circulation of these cells to other organs. In one embodiment, a catheter device includes expandable occlusion elements in the form of inflatable balloons that can be used to isolate a proximal and distal end of a pancreatic portion of the splenic artery. In another embodiment, the occlusion elements include a filter element instead of a balloon. In some embodiments, targeted delivery of stem cells to the pancreatic tail can be achieved for treatment of, for example, diabetes. In some embodiments, an arterial section of the splenic artery can be isolated for selective perfusion of therapeutic cells/drugs to the tail of the pancreas.

8 Claims, 11 Drawing Sheets

(56) References Cited

U.S. PATENT DOCUMENTS

| | | |
|---|---|---|
| 4,883,459 A | 11/1989 | Calderon |
| 5,281,200 A | 1/1994 | Corso, Jr. et al. |
| 5,318,535 A | 6/1994 | Miraki |
| 5,338,301 A | 8/1994 | Diaz |
| 5,397,307 A | 3/1995 | Goodin |
| 5,415,636 A | 5/1995 | Forman |
| 5,419,763 A | 5/1995 | Hildebrand |
| 5,462,529 A | 10/1995 | Simpson et al. |
| 5,478,309 A | 12/1995 | Sweezer et al. |
| 5,484,412 A | 1/1996 | Pierpont |
| 5,514,092 A | 5/1996 | Forman et al. |
| 5,575,815 A | 11/1996 | Slepian et al. |
| 5,772,632 A | 6/1998 | Forman |
| 5,810,757 A | 9/1998 | Sweezer, Jr. et al. |
| 5,833,644 A | 11/1998 | Zadno-Azizi et al. |
| 5,833,650 A | 11/1998 | Imran |
| 5,833,672 A | 11/1998 | Kawata et al. |
| 5,836,905 A | 11/1998 | Lemelson et al. |
| 5,836,967 A | 11/1998 | Schneider |
| 5,919,163 A | 7/1999 | Glickman |
| 5,925,016 A | 7/1999 | Chornenky et al. |
| 5,961,536 A | 10/1999 | Mickley et al. |
| 5,968,012 A | 10/1999 | Ren et al. |
| 6,030,362 A | 2/2000 | Boussignac et al. |
| 6,051,014 A | 4/2000 | Jang |
| 6,126,635 A | 10/2000 | Simpson et al. |
| 6,156,053 A | 12/2000 | Gandhi et al. |
| 6,165,152 A | 12/2000 | Becker et al. |
| 6,176,844 B1 | 1/2001 | Lee |
| 6,287,290 B1 | 9/2001 | Perkins et al. |
| 6,299,598 B1 | 10/2001 | Bander |
| 6,346,098 B1 | 2/2002 | Yock et al. |
| 6,436,090 B1 | 8/2002 | Sanchez et al. |
| 6,440,097 B1 | 8/2002 | Kupiecki |
| 6,461,327 B1 | 10/2002 | Addis et al. |
| 6,482,172 B1 | 11/2002 | Thramann |
| 6,485,500 B1 * | 11/2002 | Kokish et al. ................ 606/194 |
| 6,488,672 B1 | 12/2002 | Dance et al. |
| 6,508,777 B1 | 1/2003 | Macoviak et al. |
| 6,520,183 B2 | 2/2003 | Amar |
| 6,569,146 B1 | 5/2003 | Werner et al. |
| 6,569,148 B2 | 5/2003 | Bagaoisan et al. |
| 6,575,932 B1 | 6/2003 | O'Brien et al. |
| 6,589,264 B1 | 7/2003 | Barbut et al. |
| 6,592,546 B1 | 7/2003 | Barbut et al. |
| 6,682,499 B2 | 1/2004 | Lenker |
| 6,685,672 B1 | 2/2004 | Forman |
| 6,692,458 B2 | 2/2004 | Forman et al. |
| 6,699,231 B1 | 3/2004 | Sterman et al. |
| 6,702,781 B1 | 3/2004 | Reifart et al. |
| 6,706,013 B1 | 3/2004 | Bhat et al. |
| 6,712,806 B2 | 3/2004 | St. Germain et al. |
| 6,723,070 B1 | 4/2004 | Arai et al. |
| 6,743,196 B2 | 6/2004 | Barbut et al. |
| 6,749,581 B2 | 6/2004 | Thompson et al. |
| 6,884,233 B2 | 4/2005 | Dance et al. |
| 6,929,633 B2 | 8/2005 | Evans et al. |
| 6,939,320 B2 | 9/2005 | Lennox |
| 6,986,788 B2 | 1/2006 | Paul et al. |
| 6,997,898 B2 | 2/2006 | Forman |
| 7,150,736 B2 | 12/2006 | Barbut et al. |
| 7,179,251 B2 | 2/2007 | Palasis |
| 7,297,475 B2 | 11/2007 | Koiwai et al. |
| 7,452,532 B2 * | 11/2008 | Alt ............................... 424/93.7 |
| 7,503,904 B2 | 3/2009 | Choi |
| 7,645,259 B2 | 1/2010 | Goldman |
| 7,708,715 B2 * | 5/2010 | Gellman .................... 604/96.01 |
| 7,780,628 B1 | 8/2010 | Keren et al. |
| 7,815,624 B2 | 10/2010 | Larson |
| 7,887,661 B2 | 2/2011 | Chiu et al. |
| 8,043,257 B2 | 10/2011 | Nguyen et al. |
| 8,088,103 B2 | 1/2012 | Teeslink et al. |
| 8,162,879 B2 * | 4/2012 | Hattangadi et al. ...... 604/101.03 |
| 8,172,792 B2 | 5/2012 | Wang et al. |
| 8,177,829 B2 | 5/2012 | Benson et al. |
| 8,182,446 B2 | 5/2012 | Schaeffer et al. |
| 8,182,463 B2 | 5/2012 | Chiu et al. |
| 8,251,948 B2 | 8/2012 | Goldman |
| 8,262,611 B2 | 9/2012 | Teeslink et al. |
| 8,262,613 B2 | 9/2012 | Lennox |
| 2001/0041862 A1 | 11/2001 | Glickman |
| 2002/0082548 A1 | 6/2002 | Sanchez et al. |
| 2002/0107471 A1 | 8/2002 | Thompson et al. |
| 2002/0115982 A1 * | 8/2002 | Barbut et al. .................. 604/509 |
| 2005/0059931 A1 * | 3/2005 | Garrison et al. ......... 604/101.04 |
| 2008/0269718 A1 | 10/2008 | Wiener et al. |
| 2009/0018526 A1 | 1/2009 | Power et al. |
| 2009/0088676 A1 * | 4/2009 | Murata ....................... 604/6.16 |
| 2009/0131866 A1 | 5/2009 | Zhang et al. |
| 2009/0275918 A1 * | 11/2009 | Crocker ........................ 604/508 |
| 2011/0257577 A1 * | 10/2011 | Lane et al. ................... 604/6.11 |
| 2011/0295114 A1 * | 12/2011 | Agah et al. .................... 600/435 |

OTHER PUBLICATIONS

European Search Report for European Patent Application No. 10835110.7, mailed on Mar. 21, 2013, 10 pages.

* cited by examiner

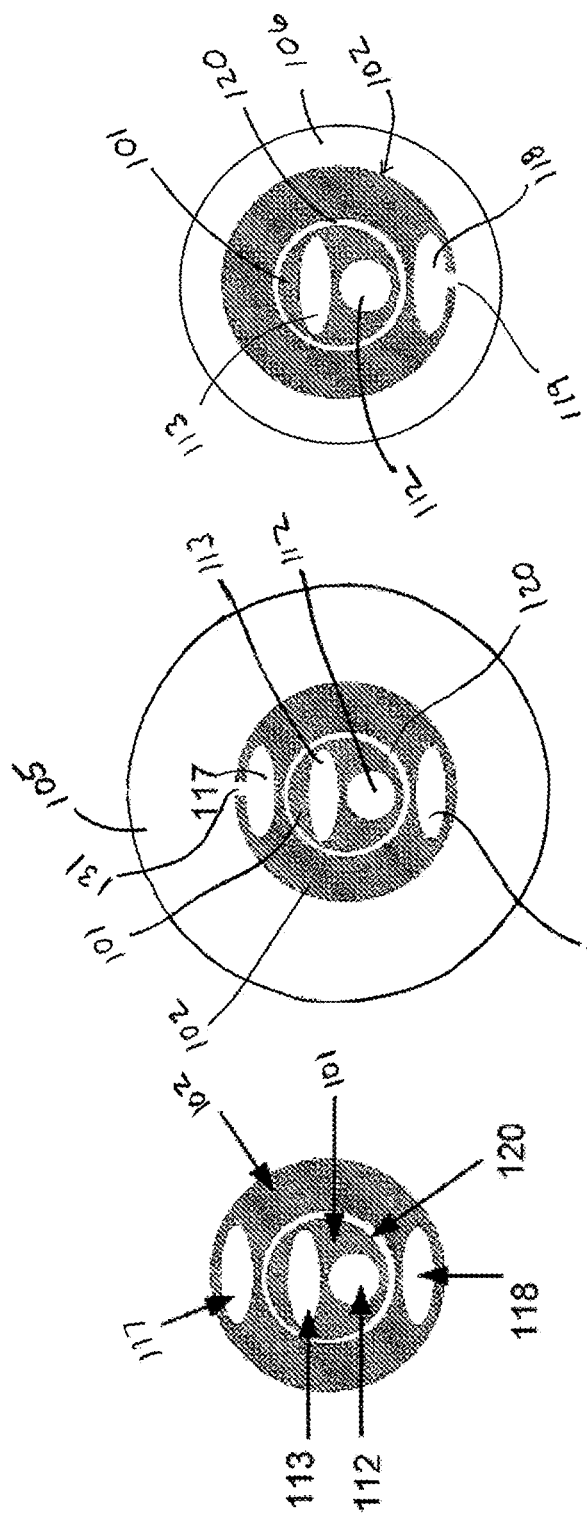

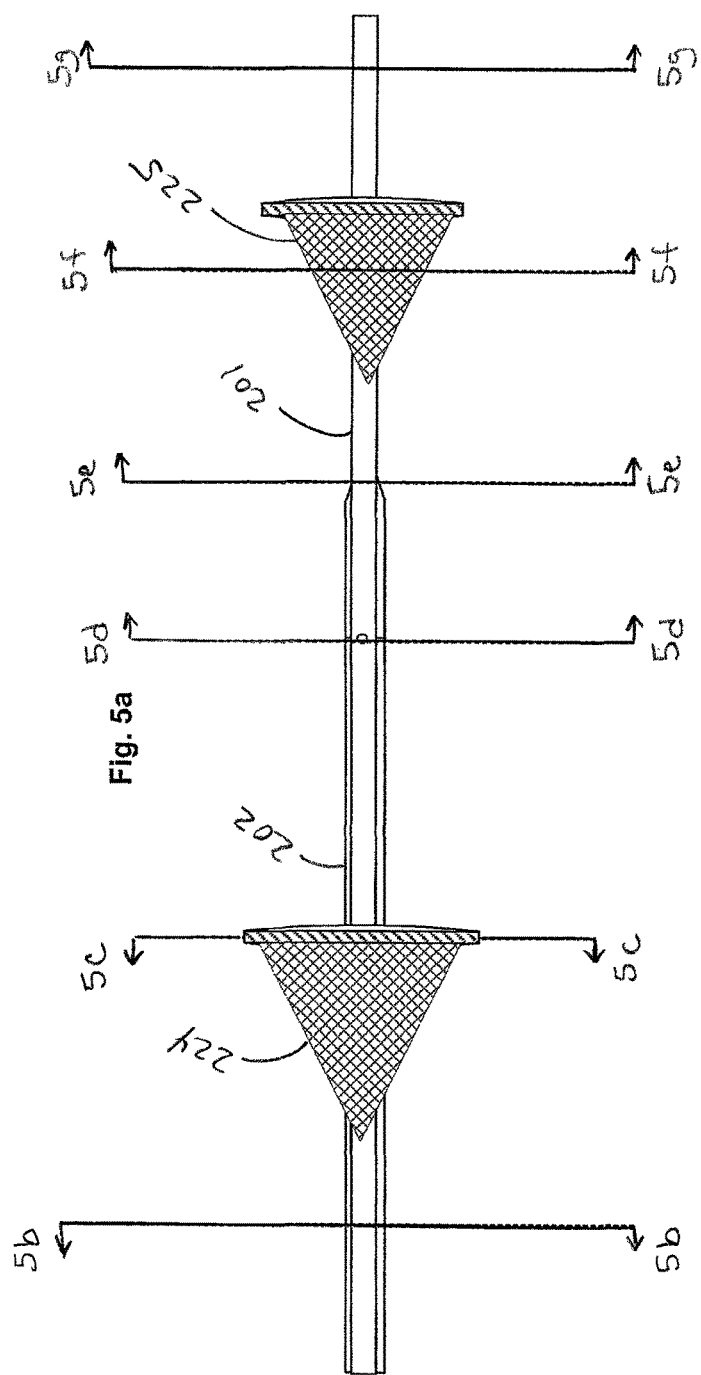

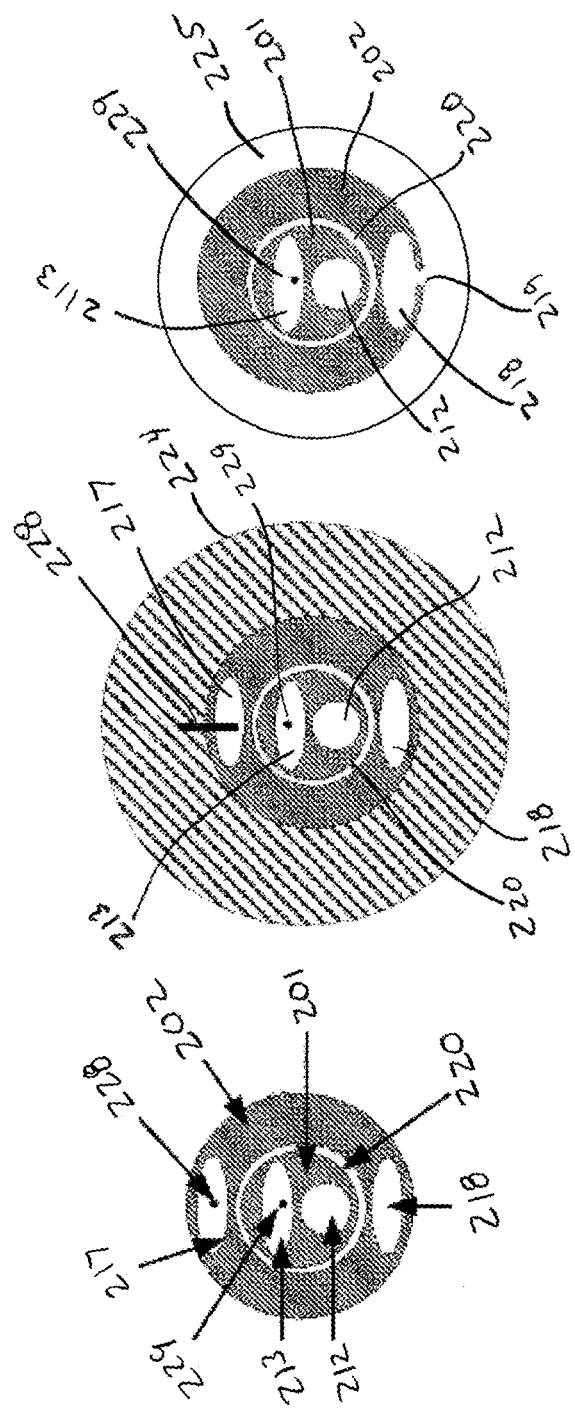

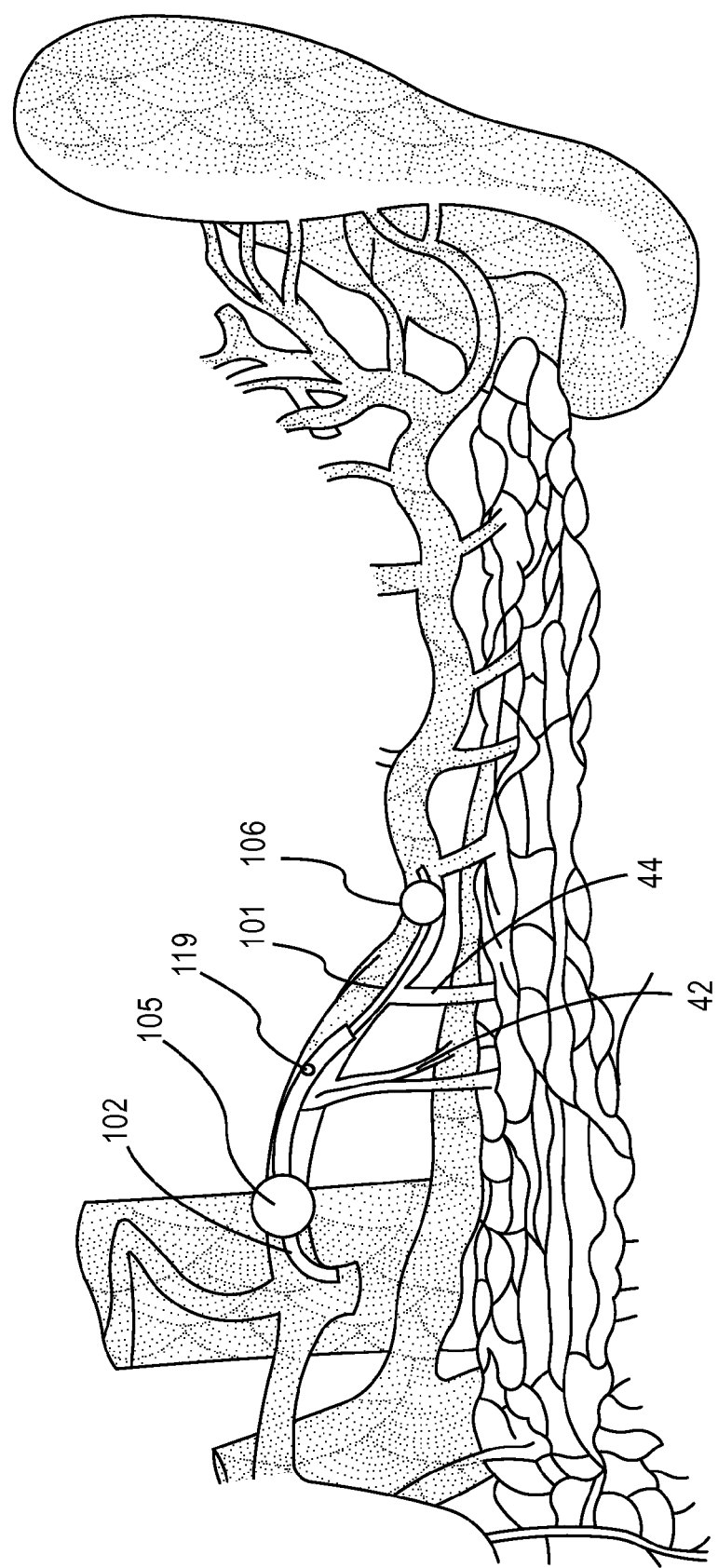

DEVICES, METHODS AND KITS FOR DELIVERY OF THERAPEUTIC MATERIALS TO A PANCREAS

CROSS-REFERENCE TO RELATED APPLICATIONS

This application claims priority to and the benefit of U.S. Provisional Patent Application No. 61/265,845, filed on Dec. 2, 2009, and entitled "A Catheter Systems Adapted for Endovascular Delivery of Therapeutic Materials to a Mammalian Pancreas, Method of Treatment of Diabetes, and Kits Therefor," the disclosure of which is hereby incorporated herein by reference in its entirety.

BACKGROUND

Diabetes is a chronic, life-threatening disease for which there is no known cure. It is a syndrome characterized by hyperglycemia and relative insulin deficiency. Diabetes affects more than 120 million people world wide, and is projected to affect more than 220 million people by the year 2020. It is estimated that one out of every three children today will develop diabetes sometime during their lifetime. Diabetes is usually irreversible, and can lead to a variety of severe health complications, including coronary artery disease, peripheral vascular disease, blindness and stroke. The Center for Disease Control (CDC) has reported that there is a strong association between being overweight, obesity, diabetes, high blood pressure, high cholesterol, asthma and arthritis. Individuals with a body mass index of 40 or higher are more than 7 times more likely to be diagnosed with diabetes.

There are two main types of diabetes: Type I diabetes (insulin-dependent diabetes mellitus) and Type II diabetes (non-insulin-dependent diabetes mellitus). Varying degrees of insulin secretory failure may be present in both forms of diabetes. In some instances, diabetes is also characterized by insulin resistance. Insulin is the key hormone used in the storage and release of energy from food.

As food is digested, carbohydrates are converted to glucose and glucose is absorbed into the blood stream primarily in the intestines. Excess glucose in the blood, e.g., following a meal, can stimulate insulin secretion, which can promote entry of glucose into the cells, and which controls the rate of metabolism of most carbohydrates.

Insulin secretion functions to control the level of blood glucose both during fasting and after a meal, to keep the glucose levels at an optimum level. In a person without diabetes, blood glucose levels are typically between 80 and 90 mg/dL of blood during fasting and between 120 to 140 mg/dL during the first hour or so following a meal. For a person with diabetes, the insulin response does not function properly (either due to inadequate levels of insulin production or insulin resistance), resulting in blood glucose levels below 80 mg/dL during fasting and well above 140 mg/dL after a meal.

Currently, persons suffering from diabetes have limited options for treatment, including taking insulin orally or by injection. In some instances, controlling weight and diet can impact the amount of insulin required, particularly for non-insulin dependent diabetics. Monitoring blood glucose levels is an important process that is used to help diabetics maintain blood glucose levels as near as normal as possible throughout the day.

Self administration of insulin is not only inconvenient but also associated with significant morbidity and other safety concerns. Hence transplant of insulin producing beta cells in the pancreas has been attempted as a form of therapy, but with less success due to limited supply and long term need for immunosuppression. Recently, transplantation of autologous stem cells (mesenchymal, bone marrow, and others) have been proposed to increase/replace the supply of insulin. Early results are encouraging, especially in Type II diabetes where auto-immune reaction against these cells appears limited.

Nevertheless, to date uniformity in the best method for transplanting such cells has not been reached. Various methods that have been applied include, for example, transplanting the cells surgically in the sub capsular space in the kidney, the liver, and non selective systemic injection both intravenously and intra-arterially, with the hope of "homing" these cells to the pancreatic tissue, to allow engraftment.

The long term success of any approach for delivering transplanted cells will be dependent on the ability of these cells to differentiate into functioning beta cells in the pancreas, and allowing their survival in a supporting milieu. There are numerous reports that suggest the pancreas itself is the best target for the transplanted cells to meet both of these objectives. So far efforts have included sub-selective endovascular injection of these cells into the arterial supply of the pancreatic tissue. Such an approach is subject to significant variation in the number of cells actually introduced to the pancreas (versus other organs in the same vascular bed including the spleen, the liver and the stomach). Furthermore, safety issues have been raised/reported when these cells were inadvertently targeted to other organs. How to best achieve successful engraftment of these cells into the pancreatic tissue is presently a limitation of some of these early studies; even though long term success of the technique appears to be directly correlated with the efficiency of the engraftment.

The present state of the art would benefit from a method where these cells can be targeted selectively to the pancreas, where efficient and safe engraftment can be achieved, especially to the pancreatic tail, where a large number of the endogenous islet cells reside, and devices and kits that are adapted to enable such methods.

In another disease process involving the pancreas, pancreatic cancer is the fourth leading cause of death from cancer, with 47,000 new cases diagnosed in the United States every year. At the time of diagnosis, only twenty percent of the patients suffering from pancreatic cancer present with localized disease amenable to surgery. Forty percent of the patients present with locally advanced (and therefore unresectable) disease, and another forty percent from distal metastasis. Pancreatic cancer is considered an almost chemoresistant tumor. The average tumor response rate with 5-FU alone, or in combination with other agents, is in the range of 7%-28%; as such systemic adjuvant chemotherapy for pancreatic cancer has not increased the 5 year survival rate. The ineffectiveness of systemic chemotherapy is at least in part due to failure to reach a drug concentration within the tumor because of dose limited toxicity in bone marrow and epithelial tissue. Since systemic chemotherapy is of limited effectiveness, approaches beyond systemic chemotherapy are needed for advanced pancreatic cancer. One promising approach is local intra-arterial delivery. In other cancers, intra-arterial chemotherapy has improved the response rates and quality of life in patients with liver metastasis and colorectal cancer.

Intra-arterial infusion allows higher drug concentration to reach the tumor, overcoming the problem of poor blood flow to tumor mass in comparison to healthy tissue. Furthermore, intra-arterial chemotherapy can also take advantage of the first pass effect of chemotherapeutics, generating higher level drug concentrations at the tumor cell membrane and therefore enhancing cellular drug uptake as compared to intravenous infusion. Lastly, local delivery can reduce systemic side effects.

The chemotherapy is usually given through catheters placed in the celiac/hepatic artery or portal vein. However, one of the major unresolved issues in pancreatic arterial infusion chemotherapy remains the optimal method of catheter placement. In fact, the tumor response rates of pancreatic arterial infusion chemotherapy can range widely, for example, from 7% to 65%, at least in part due to efficacy of drug delivery where anticancer drugs were administered via the celiac artery without assessment of drug distribution. A key issue in catheter localization is the redundant nature of blood supply to the pancreas overlapping adjacent organs. Furthermore, the small size and anatomical variability of the branches of the hepatic and splenic arteries to the pancreas precludes reproducible cannulation via interventional techniques.

A need exists for a device and method whereby biologics (i.e., chemotherapy) can selectively be targeted to the pancreas, where the therapeutic index of a drug can be enhanced by increasing local tissue concentration, with minimal dosing to the surrounding organ.

SUMMARY

Devices, kits and methods are described herein for isolating a segment(s) of the arterial system of the pancreas, and then introducing therapeutic cells/agents exclusively to a target area of the pancreatic tissue. This can be achieved by percutaneously isolating the pancreatic portion of the celiac axis via an endovascular catheter that is configured to access the target anatomy, and then exogenously introducing therapeutic cells/agents/biologics into the isolated area, via an infusion port of the catheter. In such fashion, the cells/agents biologics can be delivered to the pancreatic tail with high efficiency. In one embodiment, a device with two sliding balloon catheters can be used to isolate a target area of the splenic artery with major branches to the pancreatic tail. The isolated area can then be perfused with cells via an infusion port disposed between the two balloon catheters. In some embodiments, it may be desirable to temporarily isolate the two ends of the pancreatic section of the splenic artery by other mechanisms including, for example, micro-filters configured to prevent passage of cells, but enabling passage of other fluids.

In some embodiments, a system and/or device(s) are provided for endovascular introduction of therapeutic biologics selectively to one or more target pancreatic vessels via a splenic artery for treatment of diabetes. The introduced therapeutic biologics, such as cells, thereafter engraft to a tail or a body of a pancreas. In some embodiments, a device and/or system can include, for example, an inner catheter having a distal retractable occlusion element and an inner catheter lumen adapted and configured to introduce a guidewire, and an outer catheter having a distal retractable occlusion element, an infusion lumen adapted and configured to introduce cells to one or more target pancreatic vessels, and a lumen for slidably receiving the inner catheter. In such an embodiment, the distal retractable occlusion element of the outer catheter can be positioned proximal to the distal retractable occlusion element of the inner catheter; and a sealing element can be included that is configured to selectively isolate or seal an end of the outer catheter to prevent therapeutic biologics from entering into the lumen of the outer catheter in which the inner catheter is slidably disposed.

In some embodiments, the occlusion elements described above can be used to isolate a targeted region of the tail or body of the pancreas. In some embodiments, the infusion lumen of the outer catheter can further be configured to allow atraumatic introduction of biologics or cells, such as stem cells, into the isolated region. The infusion lumen can also be configured to allow rapid infusion of biologics or cells without causing damage to the cells during the infusion process.

In some embodiments, a selective sealing element can include, but not be limited to, a ring, a membrane, or another element configured to prevent loss of cells into the lumen of the outer catheter in which the inner catheter is disposed to maximize engraftment efficiency. As will be appreciated by those skilled in the art, any means for selectively sealing can be used without departing from the scope of the invention. The lumen provided in the inner catheter can be configured to perfuse a distal organ beyond the targeted isolation region of the artery.

In some embodiments, a distance between the proximal retractable occlusion element and the selective sealing element can be configured for external adjustment, thus allowing a user to customize the isolated area (between the two occlusion elements) to better target the tail or body of the pancreas during delivery of biologics. The proximal retractable occlusion element and the selective sealing element can have a cross-sectional diameter, for example, between 2-12 mm.

In some embodiments, the devices and methods described herein can be used for isolating the perfusion area of the pancreas for introduction for chemotherapy for treatment of pancreatic cancer or other therapeutic agents targeted to the pancreas.

In some embodiments, devices and methods described herein can be used for occlusion of a vessel segment. For example, a catheter device as described herein can be percutaneously introduced via a femoral artery and fluoroscopically guided to a splenic artery. An area or region of the pancreatic branches of the splenic artery can be isolated and a dye marker can be introduced that can demarcate where perfusion in the pancreatic tissue has occurred. The devices and methods described herein can perfuse the pancreatic tissue without perfusion of the surrounding organs such as the spleen and stomach. Further, the perfusion can occur with no back flush inside the lumen of the outer catheter in which the inner catheter is slidably disposed.

In some embodiments, methods of selectively and endovascularly introducing a biologic, such as stem cells, to one or more target pancreatic vessels via a splenic artery are provided. Endovascular delivery can be used for the treatment of diabetes and can enable engrafting of cells into the tail or body of the pancreas. In some embodiments, a method can include introducing into a patient a device that includes 1) an inner catheter having a distal retractable occlusion element and an inner catheter lumen configured to receive a guidewire, 2) an outer catheter having a proximal retractable occlusion element, an infusion lumen configured to introduce stem cells to one or more target pancreatic vessels, and a lumen for slidably receiving the inner catheter, and 3) a selective sealing element coupled to the outer catheter and configured to selectively isolate an end of the outer catheter to prevent the stem cells from flowing from an isolated region of the one or more target pancreatic vessels and into the lumen of the outer catheter in which the inner catheter is disposed. The catheter device can be advanced to a target pancreatic vessel and a target pancreatic vessel can be selectively isolated. A therapeutic biologic can then be injected into the isolated area. In some embodiments, the catheter device can be advanced to an ostium of a celiac artery. In some embodiments, it may also be desirable to inject a contrast dye into the isolated area. Use of such a contrast dye can be used to confirm isolation of a pancreatic magnum artery and a dorsal pancreatic artery prior to injecting the biologics. Suitable therapeutic biologics include, for example, stem cells.

In some embodiments, a kit for use in the treatment of diabetes is provided. In some embodiments, a kit can include a catheter device including an inner catheter having a distal retractable occlusion element and an inner catheter lumen configured to introduce a guidewire, an outer catheter having a proximal retractable occlusion element, an infusion lumen configured to introduce stem cells to the one or more target pancreatic vessels, and a lumen for receiving the inner catheter. The catheter device can also include a selective sealing element coupled to the outer catheter and configured to selectively isolate an end of the outer catheter to prevent the stem cells from leaving an isolated region of the one or more target pancreatic vessels from flowing into the lumen of the outer catheter in which the inner catheter is disposed. In some embodiments, such a kit can also include one or more of each of a biologic agent for delivery to a pancreas, a stylet, a dilator, a guidewire, a guide catheter, capsules for direct connection of biological materials/cells to an infusion port of a delivery catheter, a manometer to monitor a pressure in an isolated area, and/or a pump to regulate the infusion rate of cells/biologics.

In some embodiments, a catheter device is provided for isolating major branches to cancerous tissue residing in the pancreas. This can be achieved through isolation of the splenic artery, but may also apply to the hepatic artery and or superior mesenteric artery, which supply the head of the pancreas via branches to the pancreas. By selective isolation of branches to the pancreas, higher concentrations of chemotherapy can be delivered locally to the tumor.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIGS. 3b, 3c, 3d, 3e, 3f and 3g are each a cross-sectional view taken along lines, 3b-3b, 3c-3c, 3d-3d, 3e-3e, 3f-3f, 3g-3g, respectively in FIG. 3a.

FIG. 5a is a side view of a portion of the dilation catheter of FIG. 4.

FIGS. 5b, 5c, 5d, 5e, 5f and 5g are each a cross-sectional view taken along lines, 5b-5b, 5c-5c, 5d-5d, 5e-5e, 5f-5f, 5g-5g, respectively in FIG. 5a.

FIG. 6 illustrates an embodiment of a dilation catheter (using balloons as the occluding elements) shown in situ of the splenic artery.

DETAILED DESCRIPTION

As will be appreciated by those skilled in the art, the devices, treatments, methods and kits described herein can be applied to any mammal diagnosed with a disease affecting the pancreas, such as diabetes. This can include, for example, dogs, cats, and primates. However, for ease of illustration, and in view of the rate of incidence of diabetes in humans, description of the invention is provided with respect to the treatment of a human.

Devices and methods are described herein for effective engraftment of stem cells into the pancreas using an endovascular approach. Targeted intra-arterial injection of stem cells selectively in the splenic artery can achieve engraftment of insulin producing cells in the tail of the pancreas with high efficiency and without the systemic circulation of these cells to other organs. In some embodiments, a balloon catheter can be used to isolate the proximal and distal end of a pancreatic portion of the splenic artery. In another embodiment, a filter basket or element can be used in lieu of a balloon. Using such an endovascular approach, targeted delivery of stem cells to the pancreatic tail can be achieved for treatment of, for example, diabetes. In some embodiments, an arterial section of the splenic artery can be isolated for selective perfusion of therapeutic cells/drugs to the tail of the pancreas. One application of such a device and method includes the introduction of stem cells to the pancreatic tail in treatment of diabetes. Another application can include delivery of chemotherapeutic agents locally for treatment of pancreatic cancer.

Figure 1:
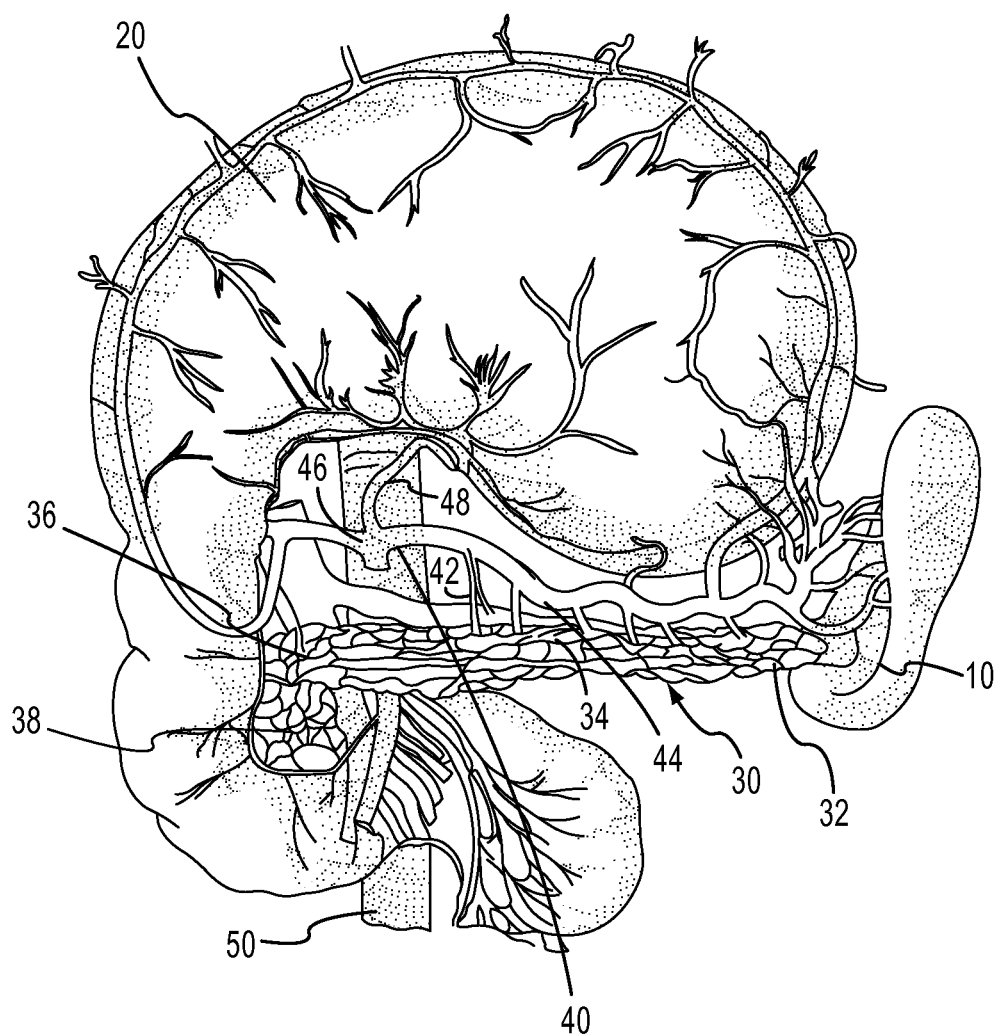
FIG. 1 is an illustration of a pancreas and related structure in a human.

FIG. 1 illustrates the spleen 10, the stomach 20, and the pancreas 30 situated within an abdominal cavity of a mammal. The pancreas 30 is a gland organ which is part of the digestive and endocrine system of vertebrates. The pancreas 30 is both an endocrine gland producing several important hormones, including insulin, glucagon, and somatostatin, as well as an exocrine gland, secreting pancreatic juice containing digestive enzymes that pass to the small intestine. These enzymes help in the further breakdown of the carbohydrates, protein, and fat in the chyme. The pancreas 30 further comprises a tail 32, a body 34, a neck 36 and a head 38.

Arterially, the pancreas 30 is accessed by the splenic artery 40, which originates from the abdominal aorta 50 and further includes four segments: 1) Pre-pancreatic, 2) Pancreatic, 3) prehilar, and 4) hilar. As will be appreciated by those skilled in the art, there is wide variability to the length of the total artery and each respective segment. Furthermore, there is also variation in the actual location and presence of major branches of this artery supplying the pancreatic parenchyma. Up to 67% of the time the dorsal pancreatic artery 42 is the major branch supplying the pancreatic body that arises from the pancreatic and peripancreatic portion of the splenic artery 40. Next, the pancreatic magnum artery 44, which is also referred to as the great pancreatic artery or greater pancreatic artery, and is the largest blood vessel that supplies oxygenated blood to the pancreas, arises from the second segment of the splenic artery 40 supplying anterior portion of the pancreatic tail 32. These two arteries form an arch anastomosis in the pancreas. There is variability in the take off of both arteries. The dorsal pancreatic artery 42 can arise from the celiac trunk 46 and or splenic artery 40 the majority of the time, and less so from superior mesenteric artery (not shown). The pancreatic magnum artery 44 commonly branches from the splenic artery 40, but can branch from a variety of locations along approximately a 15 cm length spanning the proximal to distal end of the splenic artery 40. Furthermore, each of these arteries can in turn have multiple branches/takeoffs that arise from them. Lastly, in the course of the pancreatic portion of the splenic artery 40, other arteries arise from it that supply other organs including, for example, the accessory left gastric artery 48 supplying the stomach, and the arteries supplying the spleen. The anatomical variability in the individual arteries described above requires whatever system used to allow for: (1) visualization of the common branches in this area, and (2) flexibility in the isolated distance to allow for the individual variation in the origin, exclusion of the non-pancreatic branches, and the multiple possible takeoffs of the dorsal pancreatic artery 42 or pancreatic magnum artery 44. Additionally, devices can be adapted to enable delivery of a target biologic, such as insulin producing beta cells, and autologous stem cells (mesenchymal, bone marrow, and others). Beta cells are a type of cell in the pancreas in areas called the islets of Langerhans. Beta cells make and release insulin.

Figure 2:
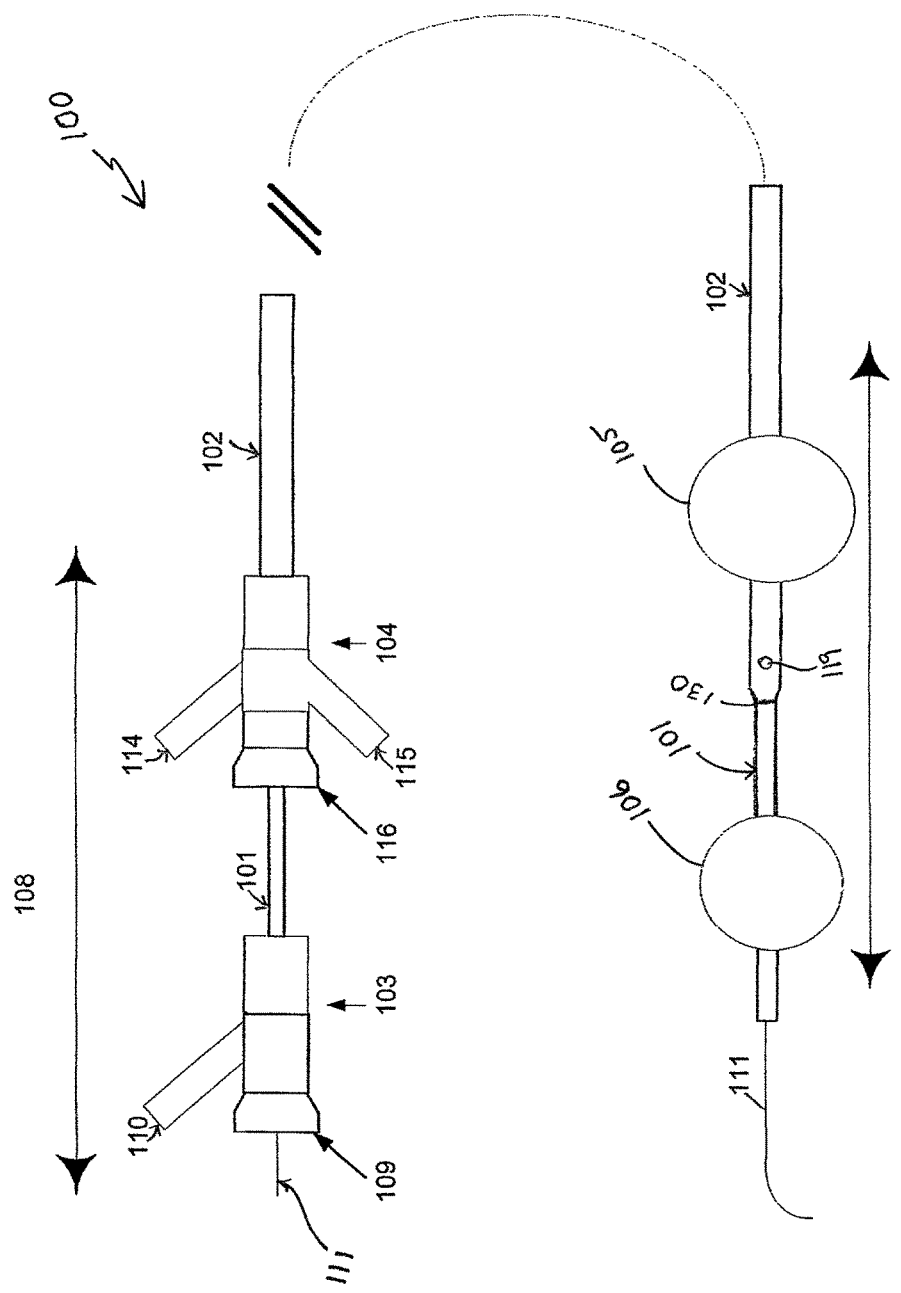
FIG. 2 is a side view of a dilation catheter, according to an embodiment and shown in a dilated configuration.

FIG. 2 is a side view of a dilation catheter device 100 (also referred to herein as "catheter device") according to an embodiment. In this embodiment, dilatation of two balloons is used to occlude a desired length of an artery such as, for example, a splenic artery. Specifically, the catheter device 100 includes a first catheter 101 (also referred to herein as "inner catheter") and a second catheter 102 (also referred to herein as "outer catheter"), a first Y-adaptor 103 and a second Y-adaptor 104 (with infusion and dilation ports described in more detail below), and a first occlusion element 106 (also referred to herein as "dilation element", "occluder" or "distal occlusion element") and a second occlusion element 105 (also referred to herein as "dilation element", "occluder" or "proximal occlusion element") each configured to occlude a portion of an artery. The second occlusion element 105 is coupled to the second catheter 102 and the first occlusion element 106 is coupled to the first catheter 101.

The occlusion elements 105 and 106 can each be moved between a collapsed configuration (also referred to as "retracted configuration") for insertion of the catheter device 100 into a body of a patient (e.g., into an artery) and an expanded configuration (also referred to as "dilated configuration" or "inflated configuration") for occluding a portion of an artery. The occlusion elements 105 and 106 when in the collapsed configuration have a smaller outer perimeter (or diameter) than when in the expanded configuration.

The catheter device 100 includes a distal end portion 107 and a proximal end portion 108. The distal end portion 107 is the end that is located furthest from a point of reference, such as an origin or a point of attachment. In this context, the distal end portion 107 would be the end farthest away from a user's hand. The proximal end portion 108, thus, would be the position nearer to a point of reference such as an origin, i.e., the user's hand.

In this embodiment, the occlusion elements 105 and 106 are expandable balloons coupled to an outer surface of the second catheter 102 and the first catheter 101, respectively, and are disposed at the distal end portion 107 of the catheter device 100. The catheter device 100 is shown in a dilated configuration in FIG. 2 with the occlusion elements 105 and 106 (i.e., balloons) in their expanded configuration (i.e., inflated, dilated).

Figure 3A:
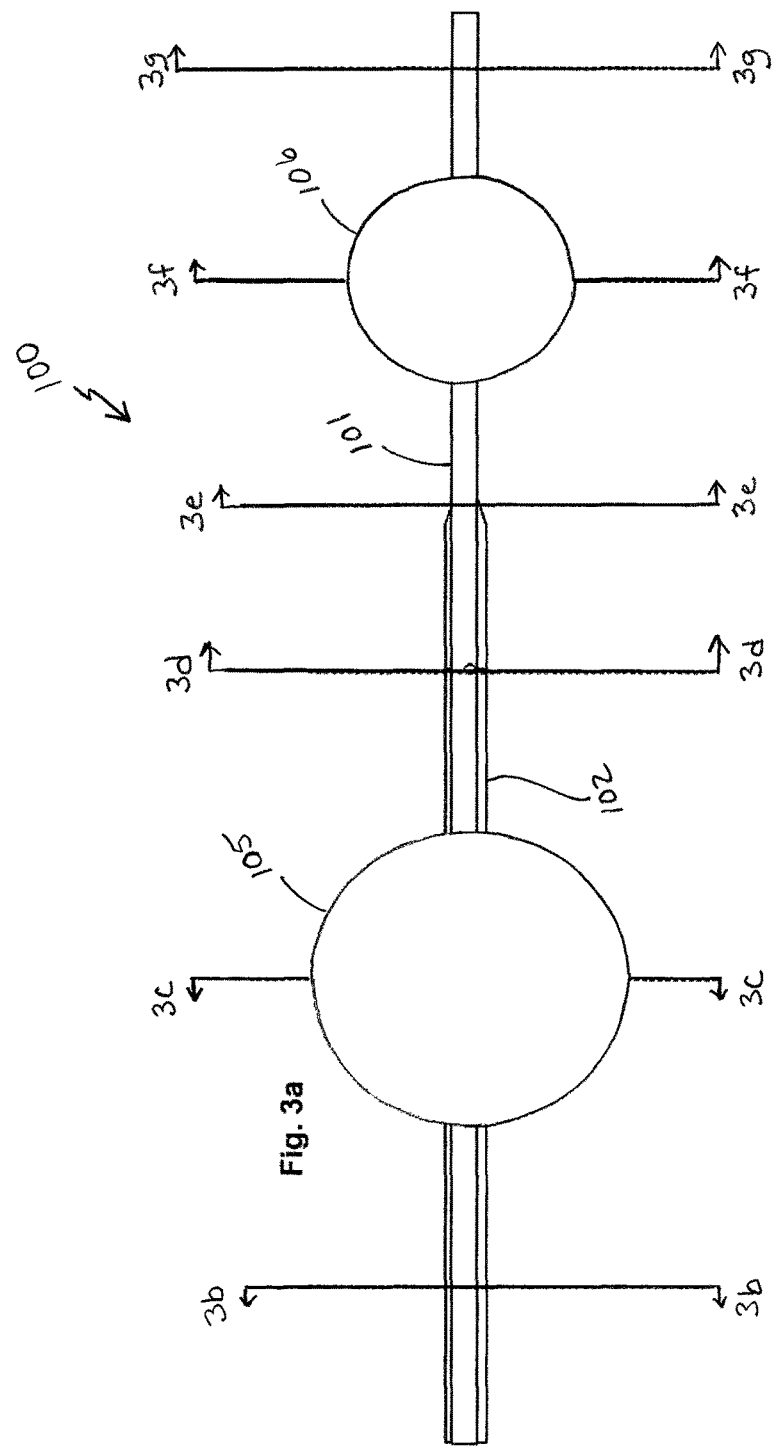
FIG. 3a is a side view of a portion of the dilation catheter of FIG. 2.
Figure 3G:
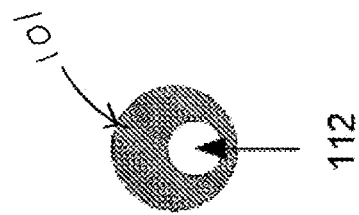
Figure 3F:
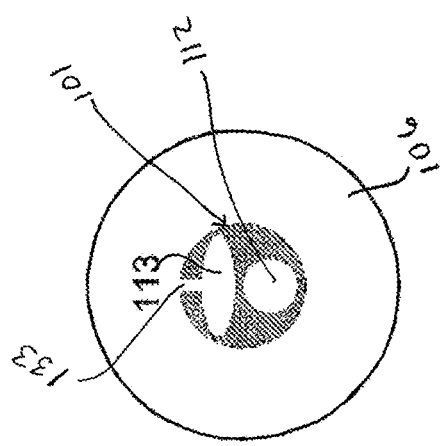
Figure 3E:
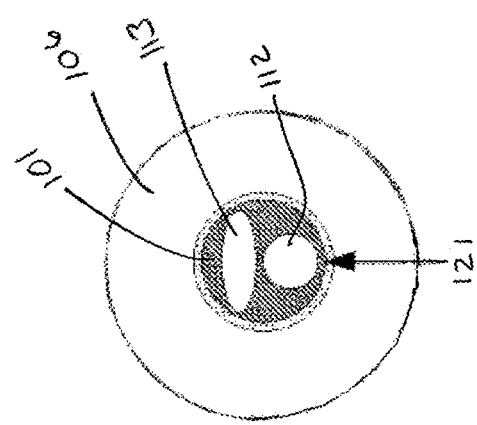

FIG. 3a is a side view of the distal end portion 107 of the catheter device 100 and FIGS. 3a-3g illustrate cross-sections at various locations along the distal end portion 107 of the catheter device 100 to illustrate the various lumens of the catheter device 100. As shown in FIGS. 3b-3g, the first catheter 101 defines a first lumen 112 and a second lumen 113 that each can extend a length of the first catheter 101. The first lumen 112 can be configured to receive a guide wire 111. The second lumen 113 can be used to communicate an inflation medium to and from the first occlusion element 106 via an aperture 133 in fluid communication with the first occlusion element 106 (see e.g., FIG. 3f).

The second catheter 102 defines a first lumen 120, a second lumen 117 and a third lumen 118. The first lumen 120 is configured to slidably receive at least a portion of the first catheter 101 therethrough. The second lumen 117 can be used to communicate an inflation medium to and from the second occlusion element 105 via an aperture 131 in fluid communication with the second occlusion element 105 (see e.g., FIG. 3c). The third lumen 118 can terminate and be in fluid communication with an infusion aperture 119 near a distal end 130 of the second catheter 102 (see, e.g., FIG. 3d). The infusion aperture 119 can be used to communicate a cell/biological material to a desired location within a body/artery of a patient.

The first Y-adaptor 103 is coupled to the first catheter 101 and includes two ports 109 and 110, as shown in FIG. 2. The port 109 is in fluid communication with the first lumen 112 of the first catheter 101 (see e.g., FIGS. 3b-3g), and can be used for introduction of the guide wire 111 into the lumen 112. Port 110 is in fluid communication with the second lumen 113 of the catheter 101 and can be used to communicate an inflation medium to the first occlusion element 106 through the second lumen 113. For example, a source of an inflation medium (not shown) can be coupled to the catheter device 100 via the port 110 of the first Y-adaptor 103.

The second Y-adapter 104 is coupled to the second catheter 102 and includes three ports 114, 115 and 116, as shown in FIG. 2. The port 116 is in fluid communication with the lumen 120 of the second catheter 102 (see e.g., FIGS. 3b-3g) and can receive the first catheter 101 therethrough. The port 114 is in fluid communication with the second lumen 117 of the second catheter 102 and can be used to communicate an inflation medium to and from the second occlusion element 105 in a similar manner as described above for port 110 and lumen 113. The port 115 is in fluid communication with the third lumen 118 of the second catheter 102 (see e.g., FIG. 3b-3g) and can be used to introduce cells/biological materials into and through the third lumen 118 and out through the infusion aperture 119.

The catheter device 100 can also include a seal element 121 (also referred to a as a "seal", "sealing element", "selective sealing element", or "filter-ring") disposed at or near a distal end 130 of the second catheter 102. The seal element 121 can prevent the entry of cells and or biologics that have been injected into an artery from flowing back into the lumen 120. By doing so, a maximum number of cells can be delivered to the treatment area, and improve engraftment efficiency. The seal element 121 can be for example, a ring, a membrane or other known sealing elements used in medical devices.

The slidable coupling of the first catheter 101 within the lumen 120 of the second catheter 102 allows a collective length of the first catheter 101 and the second catheter 102 to be adjusted by slidably moving the first catheter 101 and the second catheter 102 relative to each other. Because the first occlusion element 106 is coupled to the first catheter 101 and the second occlusion element 105 is coupled to the second catheter 102, the slidable adjustment of the first catheter 101 and the second catheter 102 can thus allow adjustment of a distance between the second occlusion element 105 and the first occlusion element 106. The lumen 120 of the second catheter 102 can be sized to receive the first catheter 101 with sufficient clearance to allow for ease of sliding/adjustment.

In use, the catheter device 100 can be placed at a desired location within an artery, such as for example, within a splenic artery 40 (see e.g., FIG. 1) and used to infuse a cell/biological material to a pancreas 30. A length of the first catheter 101 and the second catheter 102 can be adjusted such that a selected portion (e.g., a pancreatic portion) of the splenic artery 40 is isolated between the second occlusion element 105 and the first occlusion element 106. A cell/ biologic material can be injected through the catheter device 100 and into the isolated region of the splenic artery 40.

The infusion of a cell/biological agent can occur in the localized region surrounding the isolated region or segment of vessel 40. It should be noted, however, that the presence of one or more additional, side-branching vessels forming a flow restricting configuration in the isolated region of vessel 40 can allow infusion to occur in a larger semi-localized region. To allow the operator to accommodate the location of these side branches to fall within the isolated region, the first catheter 101 can be configured such that it is slidably associated with the second catheter 102 and the space between (e.g., distance between) occlusion elements 105 and 106 can be varied according to the circumstances of the desired treatment. The positioning of the distal occlusion element 106 within an artery can be individualized based on the specific anatomy to allow an enclosed or isolated area between the two occlusion elements 105 and 106 with a linear length ranging, for example, from 3 cm to 12 cm.

The cells targeted to the pancreas 30 can be infused through infusion port 115, traverse through the lumen 118 and exit through aperture 119 into the area isolated between the two occlusion elements 105 and 106. The catheter device 100 can be configured to enable delivery of target cells, such as insulin producing beta cells, and autologous stem cells (mesenchymal, bone marrow, and others) to blood vessels in communication with the pancreas in situ. The infusion pressure in the isolated blood vessel region is preferably measured with the pressure monitoring through the infusion lumen of the catheter (with a monometer (not shown) in line with infusion port 115). The pressure in the lumen can be based on the size of the cells being delivered, on the flow rate, the viscosity of the solution, and/or flow resistance of the lumen 118 of catheter 102. The flow resistance of the catheter device 100 can in turn be determined based on, for example, the inner coating material, the size and the length of the infusion lumen 118, the size of the infusion port 115, and/or the size of the distal infusion aperture 119. The catheter device 100 can allow for rapid infusion of cells (e.g., up to 1 ml/sec). In some applications, the rapid infusion of cells can enhance uptake and eventual engraftment. Smaller aperture size (e.g., aperture 119), lumen size (e.g., 118), and increased flow resistance may cause "sludging" of cells, leading to poor intra-arterial flow and diminished uptake. Lastly, the infusion port 119 and luminal design of the catheter device 100 can be configured to minimize risk of mechanical cell damage during the infusion process.

FIG. 6 is an illustration of the catheter device 100 disposed in situ within the splenic branch of the celiac artery. As shown in FIG. 6, the occlusion elements 105 and 106 define or isolate an area of interest in between the occlusion elements 105, 106. Specifically, the region or area of interest with blood supply to the pancreas is isolated via the occlusion elements 105 and 106, spaced according to the location of the dorsal pancreatic artery 42 and the pancreatic magnum artery 44. Cells can then be introduced through the infusion port 115, through the lumen 118, and out through aperture 119, in the area isolated between the occlusion elements 105 and 106.

Figure 4:
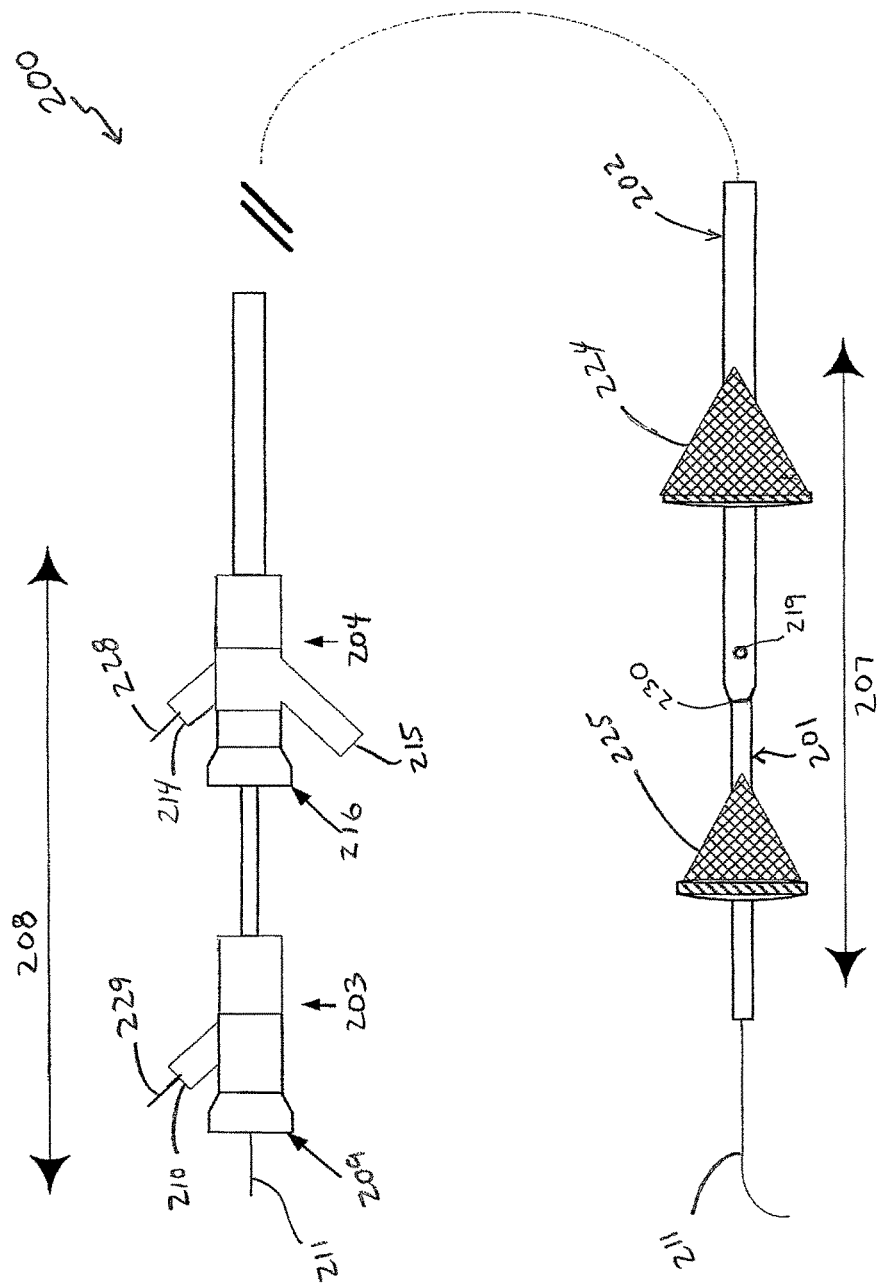
FIG. 4 is a side view of a dilation catheter, according to another embodiment.

FIG. 4 illustrates an embodiment of a catheter device 200 that uses two filter elements, instead of expandable balloons to occlude and isolate the area of interest for infusion of cells or chemotherapeutic agents, without inhibiting the flow of plasma through the isolated area. The filter elements can be formed with, for example, a medical mesh material. The size of the pores of the filter elements can be, for example, about 1 μmeter or less in length, which can inhibit cells from passing through the filter element, but not impede serum/plasma and other components from passing through the filter element. The catheter device 200 can be used for the same or similar functions as described above for catheter device 100. For example, the catheter device 200 can be used for introduction of cells into a desired location within a patient's body, such as within a splenic artery.

The catheter device 200 includes a first catheter 201 and a second catheter 202 that can be slidably coupled together as described above for catheter device 100, a first Y-adaptor 203 coupled to the first catheter 201, a second Y-adaptor 204 coupled to the second catheter 202, a first occlusion element 225 (also referred to herein as "dilation element", "occluder", "distal occlusion element") and a second occlusion element 224 (also referred to herein as "dilation element", "occluder", "proximal occlusion element") to occlude a portion of an artery. The first occlusion element 225 is coupled to the first catheter 201 and the second occlusion element 224 is coupled to the second catheter 202.

In this embodiment, the occlusion elements 225 and 224 are filter elements that can be moved between a collapsed configuration (also referred to as "retracted configuration" or "closed configuration") for insertion of the catheter device 200 into a body of a patient (e.g., into an artery) and an expanded configuration (also referred to as "dilated configuration" or "open configuration"), as shown in FIG. 4, for occluding a portion of an artery. The occlusion elements 225 and 224 when in the collapsed configuration have a smaller outer perimeter (or diameter) than when in the expanded configuration.

Figure 5G:
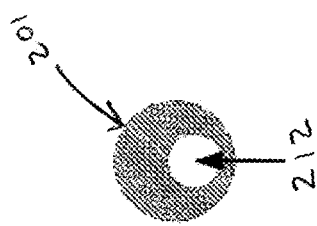
Figure 5F:
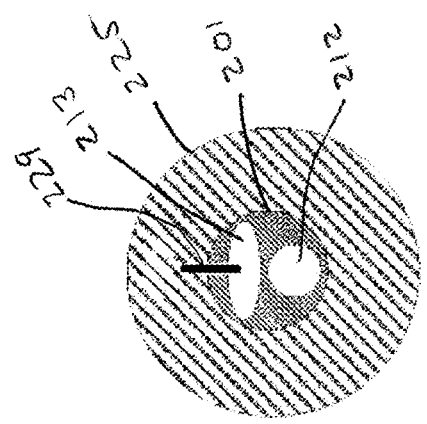
Figure 5E:
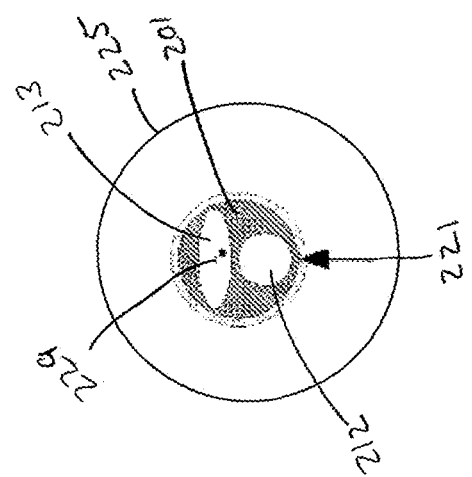

The catheter device 200 includes a distal end portion 207 and a proximal end portion 208. FIG. 5a is a side view of the distal end portion 207 of the catheter device 200 and FIGS. 5a-5g illustrate cross-sections at various locations along the distal end portion 207 of the catheter device 200. As shown in FIGS. 5b-5g, the first catheter 201 defines a first lumen 212 and a second lumen 213 that each can extend a length of the first catheter 201. The first lumen 212 can be configured to receive a guidewire 211. The second lumen 213 can be configured to receive a wire deployment device 229 that can be coupled to the filter element 225 and configured to move the filter element 225 from its expanded or open configuration and its collapsed or closed configuration.

The second catheter 202 defines a first lumen 220, a second lumen 217 and a third lumen 218. The first lumen 220 is configured to slidably receive at least a portion of the first catheter 201 therethrough, and the second lumen 217 can be configured to receive a wire deployment device 228. The wire deployment device 228 can be coupled to the filter element 224 and used to move the filter element 224 between its expanded or open configuration and its collapsed or closed configuration. The third lumen 218 can terminate and be in fluid communication with an infusion aperture 219 near a distal end of the second catheter 202. The infusion aperture 219 can be used to communicate, for example, a cell or cells to a desired location within a body of a patient.

The first Y-adaptor 203 includes, a port 209 and a port 210 as shown in FIG. 4. The port 209 is in fluid communication with the first lumen 212 of the catheter 201, and can be used for introduction of the guidewire 211 into the lumen 212. Port 210 is in fluid communication with the second lumen 213 of the catheter 201. The second Y-adapter 204 includes three ports 214, 215 and 216, as shown in FIG. 4. The port 216 is in fluid communication with the lumen 220 of the second catheter 202 and can receive the first catheter 201 therethrough. The port 214 is in fluid communication with the second lumen 217 of the second catheter 202, and the port 215 is in fluid communication with the third lumen 218 of the second catheter 202.

The filter elements 225 and 224 can each be shaped as a cone when in their expanded or open configurations as shown in FIGS. 4 and 5a. The filter elements 225 and 224 and can each be sized when in their expanded or open configurations to meet the size of a particular vessel diameter in which the catheter device 200 is to be deployed. After infusion of cells through the catheter device 200, the filter elements 224 and 225 can be collapsed to a smaller size for removal of the catheter device 200 from the patient.

In some embodiments of a catheter device (e.g., 100, 200) as described herein, a diameter of the occlusion elements (e.g., 105, 106, 225, 224) when expanded within an artery, such as, for example, a splenic artery, can be adjustable to meet anatomical variations including a) individual variability in the size of the splenic artery and b) end to end variation as the artery size can taper down between the two ends of the artery. As such, in some embodiments, to allow successful isolation of the area for treatment, the proximal occlusion element (e.g., balloon 105, filter element 224) can be sized (e.g., have an outer diameter or outer perimeter) between, for example, 2-12 mm and the distal occlusion element (e.g., balloon 106, filter element 225) between, for example, 2-12 mm. The proximal occlusion element can be larger than the distal occlusion element, smaller than the distal occlusion element, or the same size as the distal occlusion element.

Placement of the occluding elements (balloons 105, 106 or filter elements 224, 225) and the lengths of each region can be varied based on the needs of the individual application. The catheter device 100, 200 can retain sufficient trackability to allow advancement into the target region of the patient. In some embodiments, the catheter material can be flexible enough to traverse local anatomy yet have enough tensile strength to be able to be placed in position in place over a guidewire (111, 211). Furthermore, for the first and second catheters 101, 102 (or 201, 202) to be slidable relative to each other in situ, various radial and tensile strengths can be incorporated in each.

The inner catheter 101, 201 and outer catheter 102, 202 can be fabricated of any material suitable for catheters, such as linear low density or high density polyethylene, nylon, polyurethane, polypropylene, silicone rubber, or other non-thrombogenic materials. In some embodiments, a linear low density polyethylene can be used for the outer catheter 102, 202 and a nylon can be used for the inner catheter 101, 201 or the outer catheter 102, 202. In some embodiments, the outer catheter 102, 202 can be fabricated to include a structure for reinforcement (not shown), such as a metal braid located between an inner and outer layer. The reinforcement structure can extend along any desired length of the outer catheter 102, 202. In some embodiments, a reinforcement structure can extend along the entire length of the outer catheter 102, 202.

In some embodiments, regions of inner catheter 101, 201 can also be fabricated in any manner that allows the relative stiffness of each region to vary. In some embodiments, an outer layer in each region of the outer catheter 102, 202 and/or the inner catheter 101, 201 can include a material with a different durometer measurement of hardness. For example, the material used in an intermediate region can be relatively harder than that of a distal region, and the material used in a proximal region can be relatively harder than that of the intermediate region. Other manners of varying the stiffness of inner catheter 101, 201 and/or outer catheter 102, 202 are also contemplated herein, such as by varying the length of the reinforcement structure, or by varying the degree of reinforcement provided by the reinforcement structure along the length of outer catheter 102, 202 and/or the inner catheter 101, 201.

In some embodiments, radiopaque markers of gold or tantalum, for example, can also be provided on the inner catheter 101, 201 positioned within or on the occlusion elements (e.g., balloons 105, 106 or filter elements 224, 225), and/or on the outer catheter 102, 202 to aid in visualization and to assist in monitoring the position of the catheter device 100, 200 on a fluoroscope during a procedure. The inner catheter 101, 201 can optionally be coated with a lubricous material, such as silicone, acrylimide, or a hydrophilic polyurethane coating, to ease retraction. The outer catheter 102, 202 and occlusion elements (e.g., balloons 105, 106 or filter elements 224, 225) can be similarly coated to ease its advance through a guiding catheter and/or a tortuous vessel, as is known in the art.

In some embodiments, an outer diameter of the catheter device 100, 200 and the undeployed occlusion elements 105, 106 (and 224, 225) can be, for example, no greater than about 8 French, but can be, for example, as small as 6 French, so that it can be used with, for example, a 7-9 French guiding catheter (if necessary).

In some embodiments, after the guide wire 111, 211 is removed, the guide wire lumen 112, 212 can be used to establish arterial blood flow distal to the occlusion end (e.g., the distal end portion) of the catheter device 100, 200 or infusion of other therapeutic agents if desired.

As will be appreciated by those skilled in the art, suitable configurations of the catheter devices can be used to achieve the objectives described herein including, for example, employing one or more catheter devices 100, 200, employing a contiguous inflation/occluding section having differing stiffness along its length to achieve the two occluding elements, and the like. These alterations can be pursued without departing from the scope of the invention provided that the devices and systems are configured to enable delivery of the target biologic.

In some embodiments, to allow endovascular isolation of the pancreatic portion of the artery as a mechanism to achieve exclusive delivery of a therapeutic agent/cells to the pancreatic parenchyma, the catheter device (100, 200) can have the following anatomical and mechanical features:

(1) Isolation of the two ends of the pancreatic portion of the artery using two occluders (e.g., balloons 105, 106 or filters 224, 225, etc.);

(2) Adjustment of the diameter of the occluders to meet the specific anatomical needs;

(3) Adjustment of the distance between the two occluders (based on individual variation to selectively isolate for instance the portion of the splenic artery to the pancreas on one hand and maximize the perfusion area on the other hand);

(4) An infusion port where injection of contrast can be used to visualize the area of the artery isolated;

(5) Infusion port, shaft and aperture design to allow atraumatic and rapid delivery of cells/therapeutic agents; and/or (6) Recovery of the occluders along with the catheter at the end of the procedure, prior to which flushes through the infusion port can assure clearance of the cells from the isolated space.

As described herein, in some embodiments, a catheter device 100, 200 can be provided to allow the above goals to be achieved. The catheter device 100, 200 can include two catheters slidably coupled where an inner catheter defines a guide wire housing port and a distal occluder, and an outer catheter forms an infusion port and a proximal occluder, along with an inner lumen allowing the insertion of the inner catheter. The two catheters can be assembled outside the body with a distance between the two occluders set to a desired length. For example, in some embodiments, the minimum distance between the two occluders can be 3 cm, and the length can be adjusted up to a distance between the two occluders of 15 cm as needed.

In some embodiments, a catheter device described herein suitable for accessing the pancreas can include, but is not limited to, features and functions, such as, for example:

(1) Selective isolation of the targeted portion of the pancreatic portion of the artery for targeted delivery of the therapeutic agent to the pancreas.

(2) Adjustable distance between the two ends of the perfusion area to accommodate individual anatomy to allow isolation of the largest portion of the splenic artery with branches only supplying the pancreatic tail and body. If clinically indicated, the same catheter can be used to isolate portions of the hepatic artery or superior mesenteric artery supplying the head of the pancreas.

(3) An infusion port allowing first, injection of contrast into the isolated segment to allow direct visualization of the origin of the branches of the artery supplying the pancreatic tissue, and second, introduction of therapeutic drugs/cells. The dimensions and design of the infusion port and catheter shaft allowing rapid and atraumatic delivery of cells.

(4) Adjustable diameter of the proximal and distal occluders to allow both intravariable and intervariable sizes of the splenic artery.

(5) A self contained assembly unit with easy retrieval after completion of the procedure.

Figure 7:
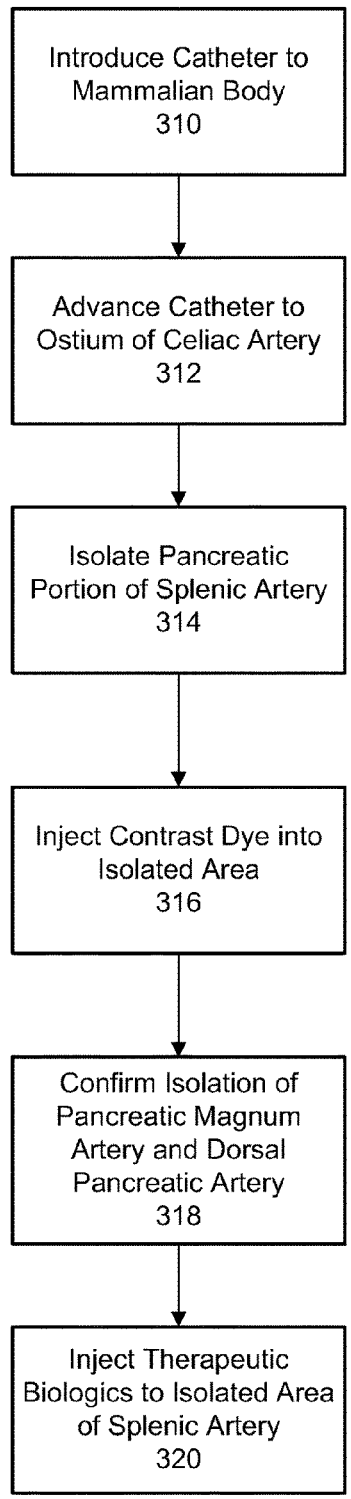
FIG. 7 is a flowchart illustrating a method for treating the pancreas, according to an embodiment.

FIG. 7 is a flowchart illustrating a method of accessing and treating a pancreas. The example method described is for occluding a portion of the splenic branch of the celiac artery supplying the pancreatic tail. A diagnostic catheter (e.g., catheter device 100, 200) is introduced into a mammalian body using standard techniques over a guide wire (111, 211) into a celiac artery at 310. The catheter device can include an inner catheter (e.g., 101, 201) slidably coupled to an outer catheter (e.g., 102, 202). In some embodiments, a guide catheter can be exchanged over the guidewire into the celiac artery for support and introduction of the catheter device. After the guidewire is in place, the catheter device can be positioned over the guidewire at 312 and positioned to allow placement of a distal occlusion element (e.g., 106, 225) of the inner catheter at a distal edge of the pancreatic portion of the splenic artery. The distal occlusion element and a proximal occlusion element (e.g., 105, 224) of the outer catheter are positioned to isolate a target portion of the pancreatic artery and moved to an expanded configuration at 314. After the occlusion elements are deployed, contrast dye is injected through an injection port of the outer catheter and the isolated area of the splenic artery is visualized to identify the pancreatic branches at 316. Visualization enables the clinician to confirm isolation of the pancreatic magnum artery and dorsal pancreatic artery or any other large artery to supplying the pancreatic body or tail in the area at 318. If desired, the catheter device can be moved back and the procedure repeated until the clinician can confirm that the catheter is correctly positioned. Some example isolation regions include: (a) the pancreatic magnum artery 44 (and its branches), (b) the dorsal pancreatic artery 42 if the origin is within the splenic artery, and (c) both pancreatic magnum artery 44 and dorsal pancreatic artery 42 arteries are isolated in one contiguous area (if other extra-pancreatic arteries do not arise between the origin of the two within the splenic artery).

After the first takeoff of the pancreatic magnum artery 44 is identified (or the dorsal pancreatic artery), the placement of the outer catheter of the catheter device can allow the edge of the distal occlusion element to be placed beyond this artery. At this point the inner catheter can be secured in place, and the outer catheter can be moved over the inner catheter to allow the maximum perfusion area to the body and tail of the pancreas. Frequent injection of contrast through the infusion port can be made to ensure no extra-pancreatic vessels are included in the isolated area.

After the desired area is isolated and the occlusion elements are positioned at a desired location, the therapeutic cells/biologics are introduced to the isolated area of the splenic artery through the infusion port of the outer catheter at 320. The infusion port design can allow rapid and atraumatic infusion of cells into the isolated area. This allows the clinician to adjust rate of infusion of therapeutic agents/cells into the isolated area based on specific pharmacodynamics and or engraftment efficiency requirements. The infusion of the cells can be followed by heparinized blood to exclude any residual cells left behind in the dead space of the catheter device. During isolation of the artery described above, perfusion to the end organ to the artery spleen can be disrupted, but the redundancy in the arterial perfusion system to the spleen, and limited time during which the arterial supply is interrupted, should prevent any long term sequela, or abnormal condition of the splenic cells. If necessary and/or desired, the guide wire port can be used to perform perfusion of the splenic artery beyond the isolated area. For example, the guidewire can be removed from its port after the catheter device is in place, and the guide wire port can be connected to a source of arterial blood with suitable pressure (i.e. the side port of an arterial sheath or guide sheath). At the end of the infusion, both occlusion elements are moved to a collapsed configuration and the catheter device is removed from the body over the guide wire as one unit, followed by the guide wire and the guide catheter.

In a variation of the above described method using occluding balloons, the same catheter can be used to isolate arterial branches supplying the head of the pancreas via the hepatic artery or superior mesenteric artery. One such clinical possibility is treatment of pancreatic cancer with the tumor located in the head of the pancreas. After placement of the catheter device in the respective artery, the infusion of contrast through the infusion port can identify the branches most proximate to the tumor, and then after occluding the distal and proximal portion of the artery around the branch(es), the chemotherapeutic agent can be delivered selectively to the area of interest in the pancreas.

In some embodiments, a method can include introducing a catheter device into a splenic artery. The catheter device can include an inner catheter, a first expandable occlusion element coupled to the inner catheter, an outer catheter defining a first lumen configured to introduce a therapeutic biologic to one or more target pancreatic vessels, a second lumen configured to slidably receive at least a portion of the inner catheter, and a second expandable occlusion element coupled to the outer catheter and disposed proximally to the first occlusion element. The catheter is advanced to a target pancreatic portion of the splenic artery. A region of the target pancreatic portion of the splenic artery is selectively isolated and the therapeutic biologic is injected into the isolated region. In some embodiments, the therapeutic biologic includes stem cells. In some embodiments, the method further includes advancing at least a portion of the catheter device to an ostium of a celiac artery, its hepatic branch, or if necessary, the superior mesenteric artery (based on individual anatomy). In some embodiments, a contrast dye is injected into the isolated region and isolation of a pancreatic magnum artery and/or a dorsal pancreatic artery can be confirmed. In some embodiments, a guidewire can be disposed through the infusion lumen to focally perforate the vascular lumen in the isolated area to increase exogenous cell penetration into the pancreatic tissue. In some embodiments, the therapeutic biologic can be introduced into the isolated segment or region to enhance cellular transmigration across the endothelial cells prior to introduction of the therapeutic biologic.

The devices described herein can also be provided in a kit. In some embodiments, a kit for use in the delivery of a biological agent to an area proximal to the pancreas can include, for example, one or more catheter devices (e.g., 100, 200) as described herein and one or more biologic agents for delivery to the pancreas. The catheter devices can include, for example, a proximal end portion, a distal end portion and one or more expandable devices, such as a balloon or a filter, associated therewith. In some embodiments, the catheter device can include a first catheter configured to be slidably received within a lumen of a second catheter, a first occlusion element coupled to the first catheter and a second occlusion element coupled to the second catheter. In such an embodiment, a distance between the first and second occlusion elements can be varied or adjusted. The occlusion elements can be expandable to engage a wall of a blood vessel thereby substantially isolating an interior region of the vessel between the first and second occlusion elements. Moreover, the first and second catheters can be configured such that at least one of the first and second catheters has a lumen configured to deliver a biological agent to the isolated interior region via an infusion port. The infusion port can allow for rapid and atraumatic delivery of cells/biologics into the isolated area. In some embodiments, a pressure regulator can be provided that is configured to regulate the fluid pressure of the agent or the materials used to dilate the occlusion element(s) (e.g., in a balloon embodiment).

In some embodiments, a kit can further include one or more biologic agents for delivery to the pancreas, a stylet(s); one or more catheters adapted and configured for accessing the pancreatic vessels; a dilator; a guide wire; a guide catheter; capsules for direct connection of biological materials/cells to the infusion port of the delivery catheter; a manometer to monitor the pressure in the isolated area; and/or a pump to regulate the infusion rate of cells/biologics.

While various embodiments have been described above, it should be understood that they have been presented by way of example only, not limitation, and various changes in form and details may be made. Any portion of the apparatuses and/or methods described herein may be combined in any combination, except mutually exclusive combinations. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above.

Although various embodiments have been described as having particular features and/or combinations of components, other embodiments are possible having any combination or sub-combination of any features and/or components from any of the embodiments described herein. The specific configurations of the various components can also be varied. For example, the size and specific shape of the various components can be different than the embodiments shown, while still providing the functions as described herein. Furthermore, each feature disclosed herein may be replaced by alternative features serving the same, equivalent or similar purpose, unless expressly stated otherwise. Thus, unless expressly stated otherwise, each feature disclosed is one example only of a generic series of equivalent or similar features.

For example, although the outer catheters (e.g., 102, 202) of the catheter devices (e.g., 100, 200) include an infusion lumen and infusion port to deliver a cell/biologic material to a desired blood vessel, in other embodiments, the inner catheter (e.g., 101, 201) can include the infusion lumen. Similarly, although the guidewire lumen is described as being defined by the inner catheter (e.g., 101, 201), a guidewire lumen can be alternatively, or in addition to, included in the outer catheter (e.g., 102, 202). Thus, any of the lumens of the catheter device (e.g., 100, 200) can be defined by either the inner catheter (e.g., 101, 201) or the outer catheter (e.g., 102, 202). In another example, although shown coupled to the outer catheter (102, 202), the sealing element (e.g., 121, 221) can alternatively be coupled to the inner catheter (e.g., 101, 201).

Although the catheter device (e.g., 100, 200) was shown and described as having either two balloon occlusion elements or two filter elements, in alternative embodiments, a catheter device (e.g., 100, 200) can include a combination of occlusion elements. For example, a catheter device (e.g., 100, 200) can include one or more balloon occlusion elements (e.g., 105, 106) and one or more filter element occlusion elements (e.g., 224, 225).

What is claimed is:

1. A method, comprising:
    introducing a catheter device into a splenic artery, the catheter device including an inner catheter, a first expandable occlusion element coupled to the inner catheter, an outer catheter defining a first lumen configured to introduce a therapeutic agent to one or more target pancreatic arteries, a second lumen configured to slidably receive at least a portion of the inner catheter, and a second expandable occlusion element coupled to the outer catheter and disposed proximally to the first occlusion element,
    advancing the catheter device to a target pancreatic portion of the splenic artery;
    selectively isolating a region of the target pancreatic portion of the splenic artery;
    confirming isolation of at least one of a pancreatic magnum artery and a dorsal pancreatic artery; and
    injecting the therapeutic agent into the isolated region.

2. The method of claim 1, further comprising:
    advancing at least a portion of the catheter device to an ostium of a celiac artery, a hepatic branch of the celiac artery or a superior mesenteric artery.

3. The method of claim 1, further comprising:
    injecting a contrast dye into the isolated region.

4. The method of claim 1, wherein the therapeutic agent includes stem cells.

5. A method, comprising:
    introducing a catheter device into a splenic artery, the catheter device including an inner catheter, a first expandable occlusion element coupled to the inner catheter, an outer catheter defining a first lumen configured to introduce a therapeutic agent to one or more target pancreatic arteries, a second lumen configured to slidably receive at least a portion of the inner catheter, and a second expandable occlusion element coupled to the outer catheter and disposed proximally to the first occlusion element,
    advancing the catheter device to a target pancreatic portion of the splenic artery;

selectively isolating a region of the target pancreatic portion of the splenic artery;

injecting the therapeutic agent into the isolated region; and inserting a guidewire through the first lumen of the outer catheter and focally perforating the splenic artery in the isolated region to increase exogenous cell penetration into pancreatic tissue.

6. The method of claim 5, further comprising:

advancing at least a portion of the catheter device to an ostium of a celiac artery, a hepatic branch of the celiac artery or a superior mesenteric artery.

7. The method of claim 5, further comprising:

injecting a contrast dye into the isolated region.

8. The method of claim 5, wherein the therapeutic agent includes stem cells.

* * * * *